United States Patent [19]

Okuyama et al.

[11] Patent Number: 4,990,537
[45] Date of Patent: Feb. 5, 1991

[54] ANTI INFLUENZA AGENT

[75] Inventors: Akira Okuyama, Tokyo; Akira Someya, Soka; Takashi Murai, Ichikawa; Nobuo Tanaka, Tokyo, all of Japan

[73] Assignee: Banyu Pharmaceutical Co., Ltd., Tokyo, Japan

[21] Appl. No.: 369,029

[22] Filed: Jun. 21, 1989

[30] Foreign Application Priority Data

Jul. 11, 1988 [JP] Japan .................................. 63-172270
Oct. 25, 1988 [JP] Japan .................................. 63-269058

[51] Int. Cl.$^5$ .................. A61K 31/155; A61K 31/235
[52] U.S. Cl. .................................. 514/634; 514/533; 514/534
[58] Field of Search ........................ 514/634, 533, 535

[56] References Cited

U.S. PATENT DOCUMENTS 4,021,472  5/1977  Fujii et al. .............................. 560/34
4,454,338  6/1984  Fujii et al. .............................. 560/34

*Primary Examiner*—Merrell C. Cashion, Jr.
*Assistant Examiner*—G. S. Kishore

*Attorney, Agent, or Firm*—Oblon, Spivak, McClelland, Maier & Neustadt

[57] ABSTRACT

An antiviral agent which comprises a p-guanidinobenzoic acid derivative of the formula:

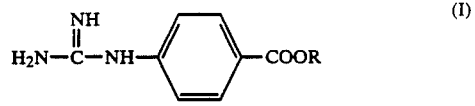

(I)

wherein R is

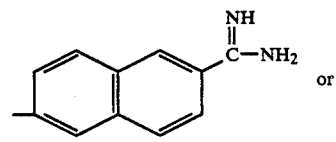

or

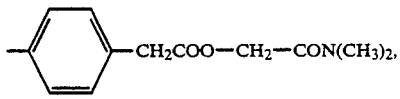

or its non-toxic salt as an active ingredient.

5 Claims, No Drawings

ANTI INFLUENZA AGENT

The present invention relates to an antiviral agent useful for treating an infectious disease caused by virus. Compounds of the formula:

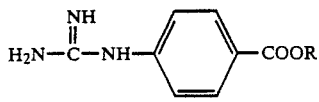

wherein R is

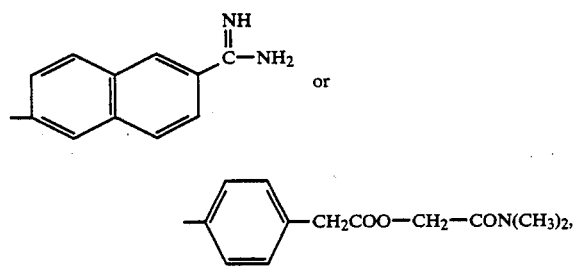

are known substances, and they are practically used in the medical field as drugs for acute symptoms of pancreatitis such as acute pancreatitis, acute deterioration of chronic pancreatitis, acute pancreatitis after surgical operation, acute pancreatitis after pancreatography and traumatic pancreatitis (Japanese Examined Patent Publications No. 41582/1979, No. 41583/1979 and No. 1063/1986, Drug Research, Vol. 13, p. 756 (1982), Biochim. Biophys. Acta., Vol. 484, p. 417 (1977), Japan J. Pharmacol., Vol. 41, p. 155 (1986) and Japan J. Pharmacol., Vol. 84, p. 363 (1984)). However, there has been no report that p-guanidinobenzoic acid derivatives of the formula I have antiviral activities.

As antiviral agents, many nucleic acid derivatives are known, and as an antiviral agent against influenza virus, amantadine is known. Antiviral agents of nucleic acid derivative type are likely to bring about side effects such as deterioration of the liver function, mutagenicity and subacute toxicity, and amantadine is likely to bring about side effects such as teratogenicity and has an undesirable characteristic such as a decrease in the reproductive efficiency (Virology, published by Raven Press, p. 323–348 (1985)). It has been desired to solve such problems inherent to the conventional antiviral agents.

As a result of extensive researches with an aim to solve such problems, the present inventors have found that a p-guanidinobenzoic acid derivative of the formula I given hereinafter or its non-toxic salt, has excellent antiviral activities and is excellent also from the aspect of the safety. The present invention has been accomplished on the basis of this discovery.

The present invention provides an antiviral agent which comprises a p-guanidinobenzoic acid derivative of the formula:

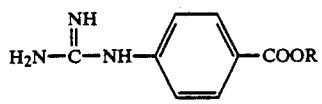

wherein R is

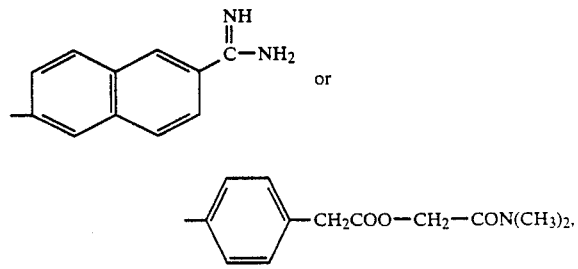

or its non-toxic salt as an active ingredient.

The present invention also provides a method for treating an infectious disease caused by a virus which comprises administering to a host infected with the virus an effective amount of the p-guanidinobenzoic acid derivative of the formula I or its non-toxic salt.

Further, the present invention provides use of the p-guanidinobenzoic acid derivative of the formula I or its non-toxic for the manufacture of an antiviral agent.

Now, the present invention will be described in detail with reference to the preferred embodiments.

Infectious diseases caused by a virus to which the antiviral agent of the present invention may be applied, iclude infectious diseases caused by envelope virus such as influenza virus, parainfluenza virus, herpes virus and human immunodeficiency virus (HIV).

The non-toxic salt of the p-guanidinobenzoic acid derivative of the formula I means a pharmaceutically acceptable salt, for example, a salt with an inorganic acid such as hydrochloric acid, sulfuric acid or phosphoric acid, or a salt with an organic acid such as acetic acid, lactic acid, citric acid, methane sulfonic acid, p-toluene sulfonic acid, succinic acid, fumaric acid or maleic acid.

The compound of the formula I of the present invention can be prepared by a known method as disclosed in e.g. Japanese Examined Patent Publications No. 41582/1979, No. 41583/1979 and No. 1063/1986.

Now, the antiviral activities of the p-guanidinobenzoic acid derivatives of the formula I will be described in detail with reference to Test Examples. However, it should be understood that the present invention is by no means restricted by such specific Examples.

TESTED COMPOUNDS

Compound A: 6-Amidino-2-naphthyl p-guanidinobenzoate dimethanesulfonate

Compound B: N,N-dimethylcarbamoylmethyl p-(p-guanidinobenzoyloxy)phenylacetate methanesulfonate

TEST EXAMPLE 1

Inhibitory Activities Against Plaque Formation of Human Influenza Virus

The inhibitory acitivities of Compounds A and B of the present invention against plaque formation of human influenza virus A/VSN were measured in accordance with the method disclosed in Virology, Vol. 29, p. 84–91 (1966).

Namely, $1 \times 10^6$ MDCK cells (dog kidney cells) were dispersed in a plastic dish having a diameter of 6 cm containing D-MEM culture medium and incubated at 37° C. for 24 hours in a $CO_2$ incubator. Then, the culture medium was discarded, and 0.1 ml of a virus-diluting solution containing about 50 influenza virus A/WSN, was added. The mixture was thoroughly shaked and left to stand at room temperature for 30 minutes, then, an agar overlay solution containing a predetermined amount of the compound to be tested, was added. After solidification of the agar, the mixture was incubated at 37° C. for three days in a $CO_2$ incubator. After incubation, the agar layer was removed, and the cells were stained with a staining solution, whereupon the plaque number was counted. As a Comparative Compound, amantadine was used. The inhibition rate against plaque formation was calculated in accordance with the following equation. The results are shown in Table 1.

$$\text{Inhibition rate (\%)} = \left(1 - \frac{T}{C}\right) \times 100$$

where

T: Average plaque number in the presence of the compound to be tested, and

C: Average plaque number in the absence of the Compound

D-MEM Culture Medium 9.5 g of 1.9% Dulbecco's Modified EAGLE MEDIUM "Nissui" powder was dissolved in 1 l of distilled water (this will be herinafter referred to 1*DMEM) and sterilized in an autoclave. Then, 0.584 g of L-glutamine sterilized by filtration, 0.1 g of kanamycin, 20 ml of a 7.5% sodium bicarbonate aqueous solution and 110 ml of a heat-activated fetal calf sera, were added thereto.

Solution for Diluting Virus

A solution is prepared by adding 10 g of calcium chloride, 10 g of magnesium chloride and 5.8 ml of 30% bovine serum albumin to 1 l of phosphate buffered saline.

| Agar overlay solution | |
|---|---|
| Pure water | 16 ml |
| 2*DMEM + BA | 50 ml |
| 1% DEAE dextran | 1 ml |
| 7.5% sodium bicarbonate aqueous solution | 2 ml |
| 2.0% agar (noble) | 30 ml |
| 2*DMEM + BA | |
| 4*Dulbecco | 250 ml |
| 1M HEPES | 10 ml |
| 10% bovine sera | 20 ml |
| 7.5% sodium bicarbonate aqueous solution | 16 ml |
| 6% glutamine aqueous solution | 10 ml |
| Kanamycin aqueous solution (100 mg/ml) | 1 ml |
| Pure water | 193 ml |

Staining Solution 100 mg of crystal violet was dissolved in 20 ml of ethanol, and 80 ml of water was added thereto.

TABLE 1

| Tested Compound | Concentration (μg/ml) | Inhibition rate (%) of plaque formation |
|---|---|---|
| Compound A | 1.0 | 19.9 |
| | 2.5 | 27.2 |
| | 5.0 | 52.1 |
| | 10.0 | 100.0 |
| | 25.0 | 100.0 |
| | 50.0 | 100.0 |

TABLE 1-continued

| Tested Compound | Concentration (μg/ml) | Inhibition rate (%) of plaque formation |
|---|---|---|
| | 100.0 | Cytotoxicity |
| Compound B | 10.0 | 29.5 |
| | 20.0 | 51.5 |
| | 40.0 | 80.5 |
| | 50.0 | 88.0 |
| | 100.0 | 100.0 |
| | 1,000.0 | 100.0 |
| Amantadine | 30.0 | 60.1 |
| | 100.0 | Cytotoxicity |

As is apparent from Table 1, Compound A of the present invention exhibited 52.1% inhibition against plaque formation of human influenza virus at a concentration of 5.0 μg/ml. Likewise, Compound B of the present invention exhibited 51.5% inhibition against plaque formation of human influenza virus at a concentration of 20 μg/ml. Further, Compounds A and B of the present invention exhibited 100% inhibition against plaque formation of human influenza virus at concentrations of 10 μg/ml and 100 μg/ml, respectively. The Comparative Compound amantadine exhibited 60.1% inhibition against plaque formation at a concentration of 30 μg/ml. Thus, Compounds A and B of the present invention have even stronger inhibitory activities against growth of human influenza virus than amantadine.

TEST EXAMPLE 2

Inhibitory Activities Against Proliferation of Human Influenza Virus (A/Fukuoka/80) in Chorioallantoic Fluid of Embryonated Chicken Eggs On the eleventh day after embryonation, 0.1 ml of a virus solution containing $6 \times 10^3$ Fukuoka virus was inoculated to the chorioallantoic fluid of embryonated chiceken eggs, and the compound to be tested was also inoculated simultaneously. The eggs were incubated for two days at 37° C. After the incubation, the eggs were kept at 4° C. overnight to kill the fetus, and the chorioallantoic fluid was sampled. The HA value of the virus was measured by using chicken erythrocytes. The results are shown in Table 2. The control group showed a HA value of 532 HA ($5 \times 10^7$ PFA/ml).

TABLE 2

| Tested Compound | Concentration for 50% inhibition against proliferation of virus (μg/ml) |
|---|---|
| Compound A | 0.125 |
| Compound B | 1.25 |
| Amantadine | >100 |

As is evident from Table 2, Compounds A and B of the present invention exhibit stronger activities for inhibiting proliferation of human influenza virus in the chorioallantoic fluid of embryonated chicken eggs than amantadine used as Comparative Example.

Further, Compounds A and B of the present invention exhibited no cytotoxicity up to concentrations of 50 μg/ml and 1,000 μg/ml, respectively, to MDCK cells (dog kidney cells) cultured for three days. Whereas, amantadine exhibited cytotoxicity slightly but distinctly even at a concentration of 30 μg/ml. Thus, Compounds A and B of the present invention have a wide range of safety as compared with amantadine.

When the compound of the formula I of the present invention is used as an antiviral agent, the dose will usually be as follows. In the case of oral administration, the compound is administered from one to three times a day with a dose of from 1 to 500 mg each time. In the case of intrarectal administration, the compound is administered from one to three times a day with a dose of from 1 to 100 mg each time. In the case of inhalation, the compound is administered into the bronchus twice or three times a day with a dose of from 0.1 to 500 mg each time. In the case of intravenous injection, the compound is administered once or twice a day with a dose of from 0.1 to 10 mg each time. In the case of intranasal administration, the compound is administered from two to four times a day with a dose of from 0.1 to 500 mg each time. As a collyrium, the compound is administered three or four times a day with a dose of from 0.1 to 50 mg each time. As an ointment, the compound is administered from one to three times a day with a dose of from 1 to 500 mg each time. However, the compound of the present invention may be used even outside these ranges depending upon the age, sex, body weight and condition of the disease of the patient.

The compound of the formula I of the present invention may be formulated into various oral or non-oral formulations by using the following additives for formulation.

Unit dosage forms for oral administration include, for example, tablets, troches, powders, pills, granules and capsules. For such dosage forms, additives, for example, a binder such as gum arabic, gelatin, sorbitol, tragacanth, polyvinyl pyrrolidone, polyvinyl alcohol, hydroxypropyl methyl cellulose, methyl cellulose, crystalline cellulose or sodium carboxymethyl cellulose, an excipient such as lactose, sugar, saccharose, sucrose, mannitol, corn starch, potassium phosphate, sorbitol or crystalline cellulose, a lubricant such as magnesium stearate, talc, polyethylene glycol or silica, and a disintegrant such as potato starch, low substitution hydroxypropyl cellulose, calcium carboxymethyl cellulose or sodium carboxymethyl starch, may be used alone or in suitable combination. Soft capsules may contain a vehicle commonly employed, such as vegetable oil, polyethylene glycol or glycerol, or an oily suspending agent given hereinafter, a solution, or a wetting agent such as a surfactant.

As a liquid formulation, there may be mentioned, for example, an aqueous or oily suspension, solution, syrup or elixir, or a dried product including a freeze-dried substance which can be dissolved in water or in other suitable vehicle at the time of its application. For such liquid formulations, additives, for example, a suspending agent such as methyl cellulose, sodium carboxymethyl cellulose, hydroxypropyl cellulose, hydroxypropylmethyl cellulose, polyvinyl pyrrolidone, polyvinyl alcohol, tragacanth, gelatin or sodium alginate, an emulsifier such as lecithin, sorbitan, a fatty acid ester, gum arabic or tragacanth, a lubricant such as a polyoxyethylene sorbitan fatty acid ester, a polyoxyethylene fatty acid ester, hydrogenated caster oil, sesami oil, soybean oil, propylene glycol, polyethylene glycol or ethyl alcohol, an antiseptic such as methyl p-hydroxybenzoate, propyl p-hydroxybenzoate or sorbic acid, and a sweetener such as a syrup, sucrose, sorbitol or mannitol, may be used alone or in suitable combination.

As the base for a drug for intrarectal administration, an oily base such as cacao butter, witepsol, or triglyceride, or a water-soluble base such as glycerol, glycerogelatin or macrogol, may be employed. As additives for an injection solution, a solublizer such as polyoxyethylene, hardened caster oil or sodiumbenzoate, an isotonic agent such as glucose, sodium chloride or glycerol, and a stabilizer such as sodium sulfite, anhydrous sodium sulfite, sodium metahydrogen sulfite or glycerol, may be used alone or in suitable combination.

For the administration to a respiratory organ such as the nose or bronchus, a formulation such as an aerosol, an inhelant, a solution, a powder, a capsule or an ointment, may be employed. In the case of an aerosol, it may be an oily aerosol formulation comprising a nonionic surfactant such as Alacel or Span 80, an amphoteric surfactant such as lecithin or a dispersant such as oleyl alcohol, a propellant such as butane or Freon ®, or an aqeous aerosol formulation comprising an isotonic agent such as physiological saline, a phosphate buffer or an acetate buffer and purified water or distilled water for injection. In the case of a solution, for example, polyethylene glycol, sorbitol, polysorbate or physiological saline may be used as the carrier for the formulation. In the case of a powder, for example, crystalline cellulose, α-cellulose, sodium crosslinked carboxymethyl cellulose, hydroxypropyl cellulose, carboxymethyl starch or amirose may be used as the carrier for the formulation. In the case of an ointment, for example, polyethylene glycol, hydroxyethyl cellulose, methyl cellulose, carboxymethyl cellulose or hydroxypropyl cellulose may be used as the carrier for the formulation.

The antiviral agent of the present invention may take a form which is applied to the mucous membrane of the oral cavity or nose so that the active ingredient is gradually released after the application. As the base to be used for such formulation, a cellulose ether such as methyl cellulose, ethyl cellulose, propyl cellulose, hydroxyethyl cellulose, carboxyethyl cellulose or hydroxypropyl cellulose, as well as polyacrylic acid or carboxyvinyl polymer, may be mentioned.

These formulations may be prepared in accordance with the respective conventional methods.

The p-guanidinobenzoic acid derivative of the present invention is contained in such formulations in an amount of from about 0.1 to 99%, preferably from 0.5 to 90%, based on the total composition.

Now, the present invention will be described in further detail with reference to Examples. However, it should be understood that the present invention is by no means restricted to such specific Examples.

EXAMPLE 1

10 g of 6-amidino-2-naphthyl p-guanidinobenzoate dimethanesulfonate, 300 g of polyethylene glycol 400 and 0.5 g of polysorbate 80 were uniformly dissolved under heating and stirring to obtain a solution for nasal application. This solution is intranasally dropwise administered in an amount of 0.1 ml each time.

EXAMPLE 2

2 g of 6-amidino-2-naphthyl p-guanidinobenzoate dimethanesulfonate was dissolved in physiological saline to obtain a solution having a total volume of 1,000 ml. This solution is put in an intranasal applicator and administered by spraying in an amount of 0.2 ml each time.

EXAMPLE 3

2 g of 6-amidino-2-naphthyl p-guanidinobenzoate dimethanesulfonate was dissolved in 500 ml of distilled water for injection heated to 50° C. To this solution, 400 ml of a 12.5% sorbitol aqeous solution was added, and the mixture was uniformly mixed and then adjusted to pH 4.0 with 0.1N hydrochloric acid. Then, distilled water for injection was added to bring the total volume to 1,000 ml to obtain a solution. This solution is put into an intranasal applicator and administered by spraying in an amount of 0.2 ml each time.

EXAMPLE 4

1.0 g of 6-amidino-2-naphthyl p-guanidinobenzoate dimethanesulfonate was pulverized in an agate mortar, and then 200 mg of Span 85 was added thereto. The mixture was uniformly kneaded. The obtained mixture was cooled to −40° C., and 10 g of a mixture of Freon 11, Freon 12 and Freon 114 in a ratio of 1:4:1 preliminarily cooled to −40° C. was mixed thereto. The mixture was filled into a pressure container at a low temperature to obtain an aerosol.

EXAMPLE 5

50 mg of 6-amidino-2-naphthyl p-guanidinobenzoate dimethanesulfonate and 450 mg of crystalline cellulose were pulverized in a mortar to obtain a uniform powder composition. This powder composition was packed in predetermined capsules to obtain capsules for pernasal administration.

EXAMPLE 6

10 mg of a freeze-dried powder of 6-amidino-2-naphthyl p-guanidinobenzoate dimethanesulfonate was dissolved in 500 ml of a 5% glucose injection solution to obtain an intravenous injection solution. This injection solution is intravenously instilled over a period of about two hours once or twice a day.

EXAMPLE 7

10 g of 6-amidino-2-naphthyl p-guanidinobenzoate dimethasulfonate, 100 g of saccharide (fine powder) and 7 g of gum arabic (fine powder) were mixed, and a proper amount of purified water was added thereto. The mixture was kneaded. The kneaded mixture was dried, and then 1 g of magnesium stearate was added thereto, followed by usual compression molding to obtain 100 troches.

EXAMPLE 8

20 g of N,N-dimethylcarbamoylmethyl p-(p-guanidinobenzoyloxy) phenylacetate methanesulfonate, 200 g of polyethylene glycol 400 and 0.5 g of polysorbate 80 were uniformly dissolved under heating and stirring to obtain a solution for nasal application. This solution is intranasally dropwise administered in an amount of 0.1 ml each time.

EXAMPLE 9

50 mg of 6-amidino-2-naphthyl p-guanidinobenzoate dimethanesulfonate and 450 mg of hydroxypropyl cellulose were thoroughly pulverized in a mortar to obtain a uniform powder composition. This powder composition was packed in predetermined capsules to obtian capsules for pernasal administration.

EXAMPLE 10

200 mg of N,N-dimethylcarbamoylmethyl p-(p-guanidinobenzoyloxy)phenylacetate methanesulfonate and 100 mg of hydroxypropyl cellulose were thoroughly pulverized in a mortar to obtain a uniform powder composition. This powder composition was packed in predetermined capsules to obtain capsules for pernasal administration.

EXAMPLE 11

50 mg of 6-amidino-2-naphthyl p-ganidinobenzoate dimethanesulfonate and 50 mg of hydroxypropyl cellulose were dissolved in 5 ml of distilled water for injection and then freeze-dried to obtain a uniform composition. This composition was packed in predetermined capsules to obtain capsules for pernasal administration.

EXAMPLE 12

50 mg of N,N-dimethylcarbamoylmethyl p-(p-guanidinobenzoyloxy)phenylacetate methanesulfonate and 50 mg of hydroxypropyl cellulose were dissolved in 5 ml of distilled water for injection and then freeze-dried to obtain a uniform composition. This composition was packed into predetermined capsules to obtain capsules for pernasal administration.

EXAMPLE 13

10 g of 6-amidino-2-naphthyl p-guanidinobenzoate dimethanesulfonate, 25 g of hydroxypropy cellulose and 20 g of Carbopol 934 were uniformly mixed. To this mixture, 0.5 g of magnesium stearate was added, followed by usual compression molding to obtain 100 flat tablets. This tablet is applied to the oral mucous membrane one tablet each time.

The compounds of the present invention are effective for inhibition against plaque formation of a virus such as human influenza virus and against proliferation of the virus in the chorioallantoic fluid of embryonated chicken eggs. Thus, the present invention contributes to the curing of infectious diseases caused by a virus.

We claim:

1. An influenza treatment composition which comprises a p-guanidinobenzoic acid derivative of the formula:

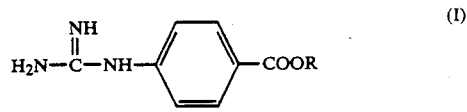

wherein R is

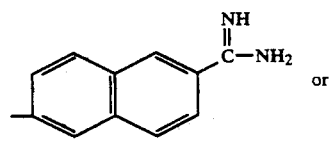

or

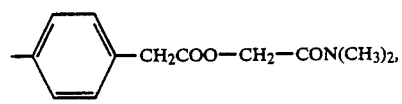

or its non-toxic salt as an active ingredient, in admixture with a pharmaceutically acceptable carrier the amount of said p-guanidinobenzoic acid derivative being effective to treat said influenza.

2. The composition according to claim 1, wherein the p-guanidinobenzoic acid derivative is 6-amidino-2-naphthyl p-guanidinobenzoate of the formula:

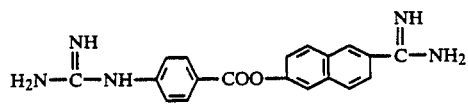
(A)

3. The composition according to claim 1, wherein the p-guanidinobenzoic acid derivative is N,N-dimethylcarbamoylmethyl p-(p-guanidinobenzoyloxy)phenylacetate of the formula:

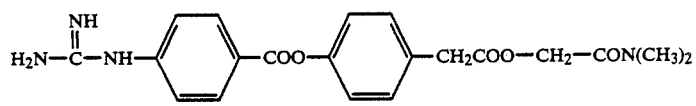
(B)

4. The composition according to claim 1, wherein the pharmaceutically acceptable carrier is a carrier for pernasal administration.

5. A method for treating influenza which comprises administering to a host in need of treatment, animal or human a p-guanidinobenzoic acid derivative of the formula:

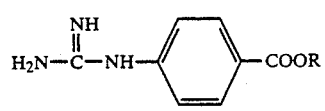
(I)

wherein R is

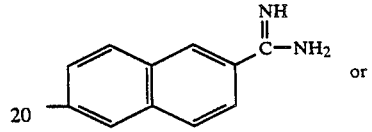
or

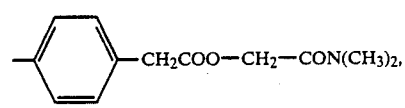

or its non-toxic salt in an amount being effective to treat said influenza.

* * * * *